United States Patent [19]

Bolich, Jr. et al.

[11] Patent Number: 5,658,557
[45] Date of Patent: Aug. 19, 1997

[54] HAIR CARE COMPOSITIONS COMPRISING SILICONE-CONTAINING COPOLYMERS

[75] Inventors: Raymond Edward Bolich, Jr., Maineville; Peter Marte Torgerson, Washington Court House, both of Ohio

[73] Assignee: The Procter & Gamble Company, Cincinnati, Ohio

[21] Appl. No.: 705,927

[22] Filed: Aug. 29, 1996

Related U.S. Application Data

[63] Continuation of Ser. No. 410,599, Mar. 27, 1995, which is a continuation of Ser. No. 253,448, Jun. 8, 1994, abandoned, which is a continuation of Ser. No. 104,232, Aug. 10, 1993, abandoned, which is a continuation of Ser. No. 758,319, Aug. 27, 1991, abandoned, which is a continuation of Ser. No. 505,755, Mar. 6, 1990, abandoned, which is a continuation-in-part of Ser. No. 390,586, Aug. 7, 1989, abandoned.

[51] Int. Cl.$^6$ .............. A61K 7/06; A61K 7/11
[52] U.S. Cl. .............. 424/70.12; 424/70.15; 424/78.03
[58] Field of Search ............. 424/70.12, 78.03, 424/70.16

[56] References Cited

U.S. PATENT DOCUMENTS

| | | | |
|---|---|---|---|
| 3,208,911 | 9/1965 | Oppliger | 167/87 |
| 3,928,558 | 12/1975 | Cheesman | 424/47 |
| 3,957,970 | 5/1976 | Korkis | 424/70 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 428/352 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,814,402 | 3/1989 | Nakashima et al. | 526/245 |
| 4,902,499 | 2/1990 | Bolich, Jr. et al. | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,166,276 | 11/1992 | Hayama et al. | 525/329 |
| 5,219,560 | 6/1993 | Suzuki et al. | 424/63 |
| 5,229,435 | 7/1993 | Sakai et al. | 523/105 |

FOREIGN PATENT DOCUMENTS

| | | | |
|---|---|---|---|
| 0 117 360 | 12/1983 | European Pat. Off. | A61K 7/06 |
| 0 408 311 A2 | 7/1990 | European Pat. Off. | C08F 230/08 |
| 56-092-811 | 7/1981 | Japan | A61K 7/11 |
| 56-129-300 | 10/1981 | Japan | A61K 7/06 |
| 4-359912 | 6/1991 | Japan | C08F 299/08 |
| 4-359913 | 6/1991 | Japan | C08F 299/08 |
| 4-360812 | 6/1991 | Japan | A61K 7/00 |
| WO88/05060 | 7/1988 | WIPO | C08F 30/08 |

*Primary Examiner*—Sallie M. Gardner
*Attorney, Agent, or Firm*—Anthony D. Sabatelli; David K. Dabbiere; Leonard W. Lewis

[57] ABSTRACT

Hair care compositions which provide improved styling and hair conditioning properties are disclosed. The compositions comprise from about 0.1% to about 10.0% of a specifically-defined silicone copolymer and from about 0.5% to about 99.5% of a carrier suitable for application to hair. These compositions are characterized by the fact that, when dried, the polymer phase separates into a discontinuous phase which includes a silicone macromer and a continuous phase which includes the copolymer backbone.

10 Claims, No Drawings

HAIR CARE COMPOSITIONS COMPRISING SILICONE-CONTAINING COPOLYMERS

This is a continuation of application Ser. No. 08/410,599, filed on Mar. 27, 1995 (currently pending), which is a continuation of application Ser. No. 08/253,448, filed on Jun. 8, 1994 (now abandoned), which is a continuation of application Ser. No. 08/104,232, filed on Aug. 10, 1993 (now abandoned), which is a continuation of application Ser. No. 07/758,319, filed on Aug. 27, 1991 (now abandoned), which is a continuation of application Ser. No. 07/505,755, filed on Mar. 6, 1990 (now abandoned), which is a continuation in part of application Ser. No. 07/390,586, filed on Aug. 7, 1989 (now abandoned).

The present invention relates to hair care compositions which have improved hair conditioning and style retention properties while still leaving the hair with a natural non-sticky feel. These compositions utilize a group of specific silicone macromer-containing copolymers.

BACKGROUND OF THE INVENTION

The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a composition to dampened hair after shampooing and/or conditioning and prior to drying and/or styling. The materials used to provide setting benefits have generally been resins or gums and have been applied in the form of mousses, gels, lotions, or sprays. This approach presents several significant drawbacks to the user. It requires a separate step following shampooing/conditioning to apply the styling composition. In addition, since the style hold is provided by resin materials which set-up on the hair, the hair tends to feel sticky or stiff after application and it is difficult to restyle the hair without further application of the styling composition.

It has now been discovered that hair care compositions comprising certain specifically-defined silicone macromer-containing copolymers provide excellent hair style retention benefits, together with hair conditioning. The compositions may be in any of the conventional forms including, but not limited to, shampoos, conditioners, hair sprays, tonics, lotions, gels, and mousses. The compositions provide these benefits to hair without leaving the hair with a stiff or sticky/tacky feel and without negatively affecting dry hair properties, such as ease of combing. Further, hair to which the compositions of the present invention have been applied may be restyled several times without requiring reapplication of the compositions.

The results are surprising since other materials which have been typically used in hair care compositions to provide style retention, such as resins and gums, generally hurt dry hair properties (e.g., combing) and leave hair with a sticky and/or stiff feel. Furthermore, silicone materials typically used for hair conditioning tend to hurt style retention.

Siloxanes (see, for example, U.S. Pat. No. 3,208,911, Oppliger, issued Sep. 28, 1965) and siloxane-containing polymers have been taught for use in hair conditioning compositions. U.S. Pat. No. 4,601,902, Fridd et al., issued Jul. 22, 1986, describes hair conditioning or shampoo/conditioner compositions which include a polydiorganosiloxane having quaternary ammonium substituted groups attached to the silicon, and a polydiorganosiloxane having silicon-bonded substituents which are amino-substituted hydrocarbon groups. U.S. Pat. No. 4,654,161, Kollmeier et al., issued Mar. 31, 1987, describes a group of organopolysiloxanes containing betaine substituents. When used in hair care compositions, these compounds are said to provide good conditioning, compatibility with anionic components, hair substantivity, and low skin irritation. U.S. Pat. No. 4,563,347, Starch, issued Jan. 7, 1986, relates to hair conditioning compositions which include siloxane components containing substituents to provide attachment to hair. Japanese Published Application 56-129,300, Lion Corporation, published Oct. 9, 1981, relates to shampoo conditioner compositions which include an organopolysiloxaneoxyalkylene copolymer together with an acrylic resin. U.S. Pat. No. 4,479,893, Hirota et al., issued Oct. 30, 1984, describes shampoo conditioner compositions containing a phosphate ester surfactant and a silicon derivative (e.g., polyether- or alcohol-modified siloxanes). Polyether-modified polysiloxanes are also disclosed for use in shampoos in U.S. Pat. No. 3,957,970, Korkis, issued May 18, 1976. U.S. Pat. No. 4,185,087, Morlino, issued Jan. 22, 1980, describes quaternary nitrogen derivatives of trialkylamino hydroxy organosilicon compounds which are said to have superior hair conditioning properties.

Siloxane-derived materials have also been used in hair styling compositions. Japanese Published Application 56-092,811, Lion Corporation, published Dec. 27, 1979, describes hair setting compositions which comprise an amphoteric acrylic resin, a polyoxyalkylene-denatured organopolysiloxane, and polyethylene glycol. U.S. Pat. No. 4,744,978, Homan et al., issued May 17, 1988, describes hair styling compositions (such as hair sprays) which include the combination of a carboxyfunctional polydimethylsiloxane and a cationic organic polymer containing amine or ammonium groups. Hair styling compositions which include polydiorganosiloxanes and a cationic organic polymer are taught in U.S. Pat. No. 4,733,677, Gee et al., issued Mar. 29, 1988, and U.S. Pat. No. 4,724,851, Cornwall et al., issued Feb. 16, 1988. Finally, European Pat. Application 117,360, Cantrell et al., published Sep. 5, 1984, discloses compositions, containing a siloxane polymer having at least one nitrogen-hydrogen bond, a surfactant, and a solubilized titanate, zirconate or germanate, which act as both a conditioner and a hair styling aid.

Siloxane-containing polymers have also been used in non-hair care applications. U.S. Pat. No. 4,136,250, Mueller et al., issued Jan. 23, 1979, relates to polymeric materials used in biological contexts where oxygen permeable and tissue compatible membranes are required. They can also be used as carriers for biologically-active substances. These materials are hydrophilic water-insoluble gels which include a low molecular weight terminal olefinic siloxane macromer and a polymer containing water-soluble monoolefinic monomer. U.S. Pat. No. 4,693,935, Mazurek, issued Sep. 15, 1987, describes pressure sensitive adhesive compositions which include a copolymer with a vinyl polymeric backbone having grafted thereto polysiloxane moieties. U.S. Pat. No. 4,728,571, Clemens et al., issued Mar. 1, 1988, relates to adhesive release coating compositions which comprise polysiloxane-grafted copolymers and blends of those copolymers with other polymeric materials. None of these last three patents suggest the use of the disclosed siloxane-containing polymers in hair care compositions.

It is an object of the present invention to formulate hair care compositions which provide effective hair conditioning and style retention properties.

It is also an object of the present invention to formulate hair care compositions which provide conditioning and style retention from a single composition.

It is a further object of the present invention to formulate hair care compositions which provide good style retention without leaving hair with a stiff or sticky/tacky feel.

It is a further object of the present invention to provide an improved method for styling and conditioning hair.

These and other objects will become readily apparent from the detailed description which follows.

Unless otherwise indicated, all percentages and ratios herein are by weight.

SUMMARY OF THE INVENTION

The present invention relates to hair care compositions comprising (a) from about 0.1% to about 10.0% of a copolymer, having a molecular weight of from about 10,000 to about 1,000,000, which has a vinyl polymeric backbone having grafted to it monovalent siloxane polymeric moieties, said copolymer comprising C monomers and components selected from the group consisting of A monomers, B monomers, and mixtures thereof wherein:

A is at least one free radically polymerizable vinyl monomer, the amount by weight of A monomer, when used, being up to about 98% of the total weight of all monomers in said copolymer;

B is at least one reinforcing monomer copolymerizable with A, the amount by weight of B monomer, when used, being up to about 98% of the total weight of all monomers in said copolymer, said B monomer being selected from the group consisting of polar monomers and macromers, preferably having a Tg or a Tm above about −20° C.; and C is a polymeric monomer having a molecular weight of from about 1,000 to about 50,000 and the general formula

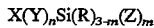

$X(Y)_n Si(R)_{3-m}(Z)_m$ wherein

X is a vinyl group copolymerizable with the A and B monomers

Y is a divalent linking group

R is a hydrogen, lower alkyl, aryl or alkoxy

Z is a monovalent siloxane polymeric moiety having a number average molecular weight of at least about 500, is essentially unreactive under copolymerization conditions, and is pendant from said vinyl polymeric backbone after copolymerization n is 0 or 1 m is an integer from 1 to 3 wherein C comprises from about 0.01% to about 50% of the copolymer;

(b) from about 0.5% to about 99.5% of a carrier suitable for application to hair.

In another embodiment, the hair care compositions of the present invention include specifically-defined phase separating copolymers of silicone with a non-silicone adhesive polymer, preferably these compositions comprise (a) from about 0.1% to about 10.0% of a silicone-containing copolymer having a vinyl polymeric backbone, preferably having a Tg above about −20° C., and having grafted to the backbone a polydimethylsiloxane macromer having a weight average molecular weight between about 1,000 and about 50,000; and (b) from about 0.5% to about 99.5% of a carrier suitable for application to hair; the polymer and carrier selected such that, when dried, the polymer phase separates into a discontinuous phase which includes the polydimethylsiloxane macromer and a continuous phase which includes the backbone.

DETAILED DESCRIPTION OF THE INVENTION

The essential, as well as the optional, components of the present invention are described below.

Silicone-Containing Copolymer

The compositions of the present invention contain from about 0.1% to about 10.0%, preferably from about 0.5% to about 8.0%, of specifically-defined silicone-containing copolymers. It is these polymers which provide the unique hair conditioning and hair setting characteristics of the present invention. The polymers should have a weight average molecular weight of from about 10,000 to about 1,000,000 (preferably from about 30,000 to about 300,000) and, preferably, have a Tg of at least about −20° C. As used herein, the abbreviation "Tg" refers to the glass transition temperature of the non-silicone backbone, and the abbreviation "Tm" refers to the crystalline melting point of the non-silicone backbone, if such a transition exists for a given polymer.

In its broadest sense, the polymers useful in the hair care compositions of the present invention include all properly defined copolymers of silicone with a non-silicone adhesive polymer. To be useful such copolymers should satisfy the following four criteria:

(1) when dried the copolymer phase-separates into a discontinuous phase which includes the silicone portion and a continuous phase which includes the non-silicone portion;

(2) the silicone portion is covalently attached to the non-silicone portion;

(3) the molecular weight of the silicone portion is from about 1,000 to about 50,000; and (4) the non-silicone portion must render the entire copolymer soluble or dispersible in the hair care composition vehicle and permit the copolymer to deposit on hair.

In addition to the graft copolymers described above, useful copolymers include block copolymers containing up to about 50% (preferably from about 10% to about 20%) by weight of one or more polydimethyl siloxane blocks and one or more non-silicone blocks (preferably acrylates or vinyls).

The most preferred polymers comprise a vinyl polymeric backbone, preferably having a Tg or a Tm above about −20° C. and, grafted to the backbone, a polydimethylsiloxane macromer having a weight average molecular weight of from about 1,000 to about 50,000, preferably from about 5,000 to about (40,000, most preferably about 20,000. The polymer is such that when it is formulated into the finished hair care composition, when dried, the polymer phase separates into a discontinuous phase which includes the polydimethylsiloxane macromer and a continuous phase which includes the backbone. It is believed that this phase separation property provides a specific orientation of the polymer on hair which results in the desired hair conditioning and setting benefits. The phase-separating nature of the compositions of the present invention may be determined as follows:

The polymer is cast as a solid film out of a good solvent (i.e., a solvent which dissolves both the backbone and the silicone). This film is then sectioned and examined by transmission electron micrography. Microphase separation is demonstrated by the observation of inclusions in the continuous phase. These inclusions should have the proper size to match the size of the silicone chain (typically a few hundred nm or less) and the proper density to match the amount of silicone present. This behavior is well documented in the literature for polymers with this structure (see, for example, S. D. Smith, Ph.D. Thesis, University of Virginia, 1987, and references cited therein).

A second method for determining phase-separating characteristics involves examining the enrichment of the concentration of silicone at the surface of a polymer film relative to the concentration in the bulk polymer. Since the silicone prefers the low energy air interface, it preferentially orients on the polymer surface. This produces a surface which is entirely covered by silicone even when the concentration of the silicone by weight in the whole polymer is low (2% to 20%). This is demonstrated experimentally by ESCA (electron spectroscopy for chemical analysis) of the dried film surface. Such an analysis shows a high level of silicone and a greatly reduced level of backbone polymer when the film surface is analyzed. (Surface here means the first few tens of Angstroms of film thickness.) By varying the angle of the interrogating beam the surface can be analyzed to varying depths.

Examples of useful copolymers and how they are made are described in detail in U.S. Pat. No. 4,693,935, Mazurek, issued Sep. 15, 1987, and U.S. Pat. No. 4,728,571, Clemens et al., issued Mar. 1, 1988, both of which are incorporated herein by reference. These copolymers are comprised of monomers A, C and, optionally, B, which are defined as follows. A is at least one free radically polymerizable vinyl monomer or monomers. B, when used, comprises at least one reinforcing monomer copolymerizable with A and is selected from the group consisting of polar monomers and macromers having a Tg or a Tm above about −20° C. when used, B may be up to about 98%, preferably up to about 80%, more preferably up to about 20%, of the total monomers in the copolymer. Monomer C comprises from about 0.01% to about 50.0% of the total monomers in the copolymer.

Representative examples of A (hydrophobic) monomers are acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5, 5,-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred A monomers include n-buryl methacrylate, isobutyl methacrylate, t-butyl acrylate, t-butyl methacrylate, 2-ethylhexyl methacrylate, methyl methacrylate, and mixtures thereof.

Representative examples of B monomers (hydrophilic) include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization) vinyl caprolactam, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof.

The C monomer has the general formula

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to about 40,000, most preferably from about 10,000 to about 20,000. Preferably, the C monomer has a formula selected from the following group:

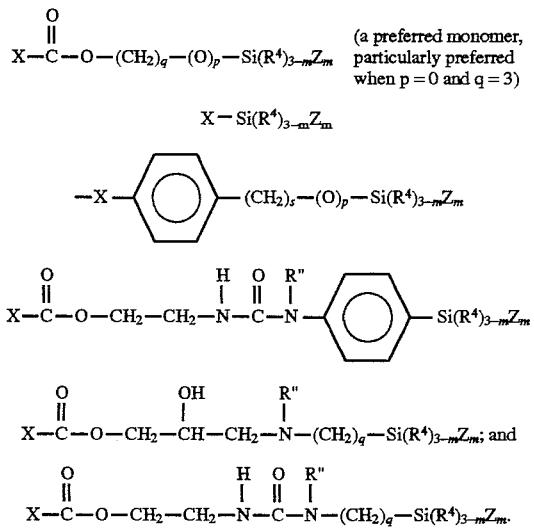

In those structures, m is 1, 2 or 3 (preferably m=1); p is 0 or 1; R" is alkyl or hydrogen; q is an integer from 2 to 6; s is an integer from 0 to 2; X is

$R^1$ is hydrogen or —COOH (preferably $R^1$ is hydrogen); $R^2$ is hydrogen, methyl or —$CH_2COOH$ (preferably $R^2$ is methyl); Z is

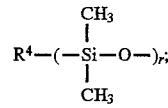

$R^4$ is alkyl, alkoxy, alkylamino, aryl, or hydroxyl (preferably $R^4$ is alkyl); and r is integer from about 5 to about 700 (preferably r is about 250).

The polymers of the present invention generally comprise from 0% to about 98% (preferably from about 5% to about 98%, more preferably from about 50% to about 90%) of monomer A, from about 0% to about 98% (preferably from about 7.5% to about 80%) of monomer B, and from about 0.01% to about 50% (preferably from about 0.5% to about 40%, most preferably from about 2% to about 25%) of monomer C. The combination of the A and B monomers preferably comprises from about 50.0% to about 99.9% (more preferably about 60% to about 99%, most preferably from about 75% to about 95%) of the polymer. The composition of any particular copolymer will help determine its formulational properties. In fact, by appropriate selection and combination of particular A, B and C components, the copolymer can be optimized for inclusion in specific vehicles. For example, pollers which are soluble in an aqueous formulation preferably have the composition: from about 0% to about 70% (preferably from about 5% to about 70%) monomer A, from about 30% to about 98% (preferably from about 30% to about 80%) monomer B, and from about 1% to about 40% monomer C. Polymers which are dispersible have the preferred composition: from about 0% to about 70% (more preferably from about 5% to about 70%) monomer A, from about 20% to about 80% (more preferably from about 20% to about 60%) monomer B, and from about 1% to about 40% monomer C.

In one aspect of the present invention, the polymers comprise from about 5% to about 98% A monomer, from about 0.01% to about 50% C monomer, and from 0% to about 98% B monomer. In these polymers, it is preferred that A be selected from t-butyl acrylate, t-butyl methacrylate, and mixtures thereof, since such polymers can be dissolved directly in cyclomethicone solvents without requiring co-solvents. This is surprising in view of U.S. Pat. No. 4,693,935 (Mazurek) and U.S Pat. No. 4,728,571 (Clemens et al), which suggest that tertiary alcohols are not suitable A monomers.

Particularly preferred polymers for use in the present invention include the following (the weight percents below refer to the amount of reactants added in the polymerization reaction, not necessarily the amount in the finished polymer):

| | |
|---|---|
| acrylic acid/n-butylmethacrylate/<br>(polydimethylsiloxane (PDMS)<br>macromer - 20,000 molecular weight) | (10/70/20 w/w/w) (I) |
| N,N-dimethylacrylamide/isobutyl<br>methacrylate/(PDMS macromer -<br>20,000 molecular weight) | (20/60/20 w/w/w) (II) |
| N,N-dimethylacrylamide/isobutyl<br>methacrylate/2-ethylhexyl<br>methacrylate/(PDMS macromer -<br>10,000 molecular weight) | (10.5/56/3.5/30<br>w/w/w/w) (III) |
| N,N-dimethylacrylamide/(PDMS macromer -<br>20,000 molecular wt) | (80/20 w/w) (IV) |
| t-butylacrylate/t-butyl methacrylate/<br>(PDMS macromer - 10,000<br>molecular wt) | (56/24/20 w/w/w) (V) |
| t-butylacrylate/(PDMS macromer -<br>10,000 molecular wt) | (80/20 w/w) (IV) |
| t-butylacrylate/N,N-dimethylacrylamide/<br>(PDMS macromer - 10,000 molecular weight) | (70/10/20) (VII) |
| t-butylacrylate/acrylic acid/<br>(PDMS monomer - 10,000 molecular weight) | (75/5/20) (VIII) |

The silicone-containing copolymers described above are synthesized as follows.

The polymers are synthesized by free radical polymerization methods, the general principles of which are well understood. See, for example, Odian, "Principles of Polymerization", 2nd edition, John Wiley & Sons, 1981, pp. 179–318. The desired monomers are all placed in a reactor, along with a sufficient amount of a mutual solvent so that when the reaction is complete the viscosity of the reaction is reasonable. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used as desired. The polymerization is allowed to proceed as long as needed for a high level of conversion to be achieved, typically from a few hours to a few days. The solvent is then removed, usually by evaporation or by precipitating the polymer by addition of a nonsolvent. The polymer is further purified, as needed.

By way of example, Polymers I, II and III, described above, are synthesized in the following manner. There are numerous variations on these procedures which are entirely up to the discretion of the synthetic chemist (e.g., choice of degassing method and gas, choice of initiator type, extent of conversion, reaction loading, etc). The choice of initiator and solvent are often determined by the requirements of the particular monomers used, since different monomers have different solubilities and different reactivities to a specific initiator.

Polymer I: Place 10 parts acrylic acid, 70 parts n-butylmethacrylate, and 20 parts 20K PDMS macromer in a flask. Add sufficient ethyl acetate to produce a final monomer concentration of 40%. Add initiator, benzoyl peroxide, to a level of 0.5% by weight relative to the amount of monomer. Evacuate the vessel, and refill with nitrogen. Heat to 60° C. and maintain this temperature for 48 hours while agitating. Terminate the reaction by cooling to room temperature, and dry off the ethyl acetate by pouring the reaction mixture into a teflon-coated pan and placing in a vacuum oven.

Polymer II: Place 20 parts N,N-dimethylacrylamide, 60 parts isobutylmethacrylate, and 20 parts silicone macromer in a reaction vessel fitted with a temperature probe, reflux condenser, inlet port, and argon sparge. Add sufficient toluene to bring the final monomer concentration to 20% by weight. Sparge with argon for 1 to 2 hours. While sparging, heat to 62° C. in a water bath. Add initiator, azobisisobutyronitrile, to a level of 0.25% by weight relative to the weight of monomer present. Maintain temperature at 62° C., with a sufficient rate of argon flow to keep the solution mixed. Monitor the reaction visually, ensuring that no phase separation of reactants occurs during polymerization. If any turbidity is observed, add sufficient warm degassed toluene to eliminate the turbidity. Continue to monitor throughout the reaction. Terminate the reaction after 4 to 6 hours and purify as with Polymer I.

Polymer III: Place 10.5 parts N,N-dimethylmethacrylamide, 56 parts isobutyl methacrylate, 3.5 parts 2-ethylhexylmethacrylate, and 30 parts 10K PDMS macromer in a reaction vessel fitted with an argon sparge, temperature probe, reflux condenser and inlet port. Add sufficient toluene or isopropanol to bring the final monomer concentration to 20% by weight. Begin stirring and sparge with argon for 1 hour. While sparging, heat to 60° C. in a water bath. Add initiator, azobisisobutyronitrile, to a level of 0.25% (if toluene is the solvent) or 0.125% (if isopropanol is the solvent) by weight relative to the weight of monomer present. Continue stirring and a slow argon sparge and maintain the reaction temperature at 60° C. Allow to react for 6 hours. Terminate the reaction and remove the solvent as with Polymer II.

Carrier

The compositions of the invention also comprise a carrier, or a mixture of such carriers, which are suitable for application to hair. The carriers are present at from about 0.5% to about 99.5%, preferably from about 5.0% to about 99.5%, most preferably from about 10.0% to about 90.0%, of the composition. As used herein, the phrase "suitable for application to hair" means that the carrier does not damage or negatively affect the aesthetics of hair or cause irritation to skin. Choice of appropriate solvent will also depend on the particular copolymer to be used, and whether the product formulated is meant to be left on hair (e.g., hair spray, mousse, tonic) or rinsed off (e.g., shampoo, conditioner) after use.

The carriers used herein include solvents, as well as other carrier or vehicle components conventionally used in hair care compositions. The solvent selected must be able to dissolve or disperse the particular silicone copolymer being used. The nature and proportion of B monomer in the copolymer largely determines its polarity and solubility characteristics. The silicone copolymers can be designed, by appropriate combination of monomers, for formulation with a wide range of solvents. Suitable solvents for use in the present invention include, but are not limited to, water, lower alcohols (such as ethanol, isopropanol), hydroalcoholic mixtures, hydrocarbons (such as isobutane, hexane, decene, acetone), halogenated hydrocarbons (such as Freon), linalool, hydrocarbon esters (such as ethyl acetate, dibutyl phthalate), volatile silicon derivatives, especially siloxanes (such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof. Preferred solvents include water, ethanol, volatile silicon derivatives, and mixtures thereof. The solvents used in such mixtures may be miscible or immiscible with each other.

Where the hair care compositions are conditioner compositions, the carrier may include gel vehicle materials. This gel vehicle comprises two essential components: a lipid vehicle material and a cationic surfactant vehicle material. Cationic surfactant materials are described in detail below. Gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000—Cetostearyl Alcohol, I. Self Bodying Action", 38 *J. of Colloid and Interface Science* 616–625 (1972).

The vehicles may incorporate one or more lipid vehicle materials which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed., 1979), incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976 (incorporated by reference herein). If included in the compositions of the present invention, the lipid vehicle material is present at from about 0.1% to about 10.% of the composition; the cationic surfactant vehicle material is present at from about 0.05% to about 5.0% of the composition.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Preferred vehicles for use in the compositions of the present invention include combinations of hydrophobically-modified hydroxyethyl cellulose materials with thickeners (such as locust bean gum), particular surfactants, quaternary ammonium compounds (such as ditallowdimethyl amonium chloride), and/or chelating agents (such as EDTA). These vehicles are described in detail in the following three concurrently-filed patent applications: Vehicle Systems for Use in Hair Care Compositions, Bolich, Norton and Russell, docket numbers 4000, 4001 and 4002, incorporated herein by reference.

Other carriers, suitable for use with the present invention are, for example, those used in the formulation of tonics, mousses, gels and hair sprays. Tonics, gels and non-aerosol hair sprays utilize a solvent such as water or alcohol while mousses and aerosol hair sprays additionally utilize a propellant such as. trichlorofluoromethane, dichlorodifluoromethane, dimethylether, propane, n-butane or isobutane. A tonic or hair spray product having a low viscosity may also require an emulsifying agent to keep the silicone copolymer homogeneously dispersed in solution. Examples of suitable emulsifying agents include nonionic, cationic, anionic surfactants, or mixtures thereof. If such an emulsifying agent is used, it is present at a level of from about 0.25% to about 7.5% of the composition. The level of propellant can be adjusted as desired but is generally from about 3% to about 30% of mousse compositions and from about 15% to about 50% of the aerosol hair spray compositions.

Optional Ingredients

The hair care compositions of the present invention may be formulated in a wide variety of product types, including mousses, gels, lotions, tonics, sprays, shampoos and conditioners. The additional components required to formulate such products vary with product type and can be routinely chosen by one skilled in the hair care product art. The following is a description of some of these additional components.

Surfactants

Surfactants are preferred optional ingredients in the compositions of the invention, particularly shampoo and conditioner compositions. When present, the surfactant comprises from about 0.05% to about 50% of the composition. For a shampoo, the level is preferably from about 10% to about 30%, most preferably from about 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants.

Synthetic anionic detergents useful herein, particularly for shampoo compositions, include alkyl and alkyl ether sulfates. These material s have the respect to the formulae $ROSO_3M$ and $RO(C_2H_4O)_xSO_3M$, wherein R is alkyl or alkenyl of from about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 10 to about 20 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species, having, for example, an average of 3 moles of ethylene oxide per mole of alcohol, is sulfated and neutralized.

Specific examples of alkyl ether sulfates which may be used in the present invention are sodium coconut alkyl triethylene glycol ether sulfate; sodium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of $\alpha$-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The $\alpha$-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific $\alpha$-olefin sulfonate mixture of the above type is described more fully in the U.S. Pat. No. 3,332,880, Pflaumer and Kessler, issued Jul. 25, 1967, incorporated herein by reference.

Another class of anionic organic surfactants are the $\beta$-alkyloxy alkane sulfonates. These compounds have the following formula:

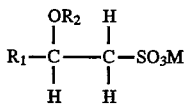

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Specific examples of $\beta$-alkyloxy-alkane-1-sulfonates, or alternatively 2-alkyloxy-alkane-1-sulfonates, having low hardness (calcium ion) sensitivity useful herein include: potassium-$\beta$-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecyl-sulfonate, sodium $\beta$-methoxyoctadecylsulfonate, and ammonium $\beta$-n-propoxydodecyl-sulfonate.

Many additional nonsoap synthetic anionic surfactants are described in *McCutcheon's, Detergents and Emulsifiers,*

1984 *Annual*, published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecydimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldimethylphosphine oxide, tetradecydimethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Among the quaternary ammonium-containing cationic surfactant materials useful herein are those of the general formula:

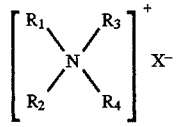

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

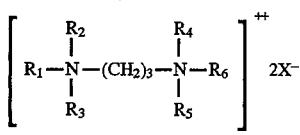

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 3981, incorporated by reference herein.

Zwitterionic surfactants, useful in shampoos as well as conditioners, are exemplified by those which can be broadly described as derivatives of aliphatic quaternary ammonium, phosphoium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

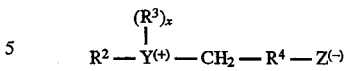

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sulfates, ethoxylated alkyl sulfates, and mixtures thereof are preferred for use herein.

The hair care compositions herein can contain a variety of other optional components suitable for rendering such compositions more cosmetically or aesthetically acceptable or to provide them with additional usage benefits. Such conventional optional ingredients are well-known to those skilled in the art, e.g., pearlescent aids, such as ethylene glycol distearate; preservatives, such as benzyl alcohol, methyl paraben, propyl paraben and imidazolidinyl urea; thickeners and viscosity modifiers, such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols, such as cetearyl alcohol; sodium chloride; sodium sulfate; polyvinyl alcohol; ethyl alcohol; pH adjusting agents, such as citric acid, sodium catrate, succinic acid, phosphoric acid, sodium hydroxide, and sodium carbonate; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin and propylene glycol. Such optional ingredients generally are used individually at levels of from about 0.01% to about 10.0%, preferably from about 0.05% to about 5.0%, of the composition.

The pH of the present compositions should be between about 3 and about 9, preferably between about 4 and about 8.

As with all compositions, the present invention should not contain components which unduly interfere with the performance of the compositions.

The hair care compositions of the present invention can be made using conventional formulation and mixing techniques. Methods of making various types of hair care compositions are described more specifically in the following examples.

Method of Use

The hair care compositions of the present invention are used in conventional ways to provide the hair conditioning/styling/hold benefits of the present invention. Such method of use depends upon the type of composition employed but generally involves application of an effective amount of the product to the hair, which may then be rinsed from the hair (as in the case of shampoos and some conditioning products) or allowed to remain on the hair (as in the case of spray, mousse, gel, and tonic products). By "effective amount" is meant an amount sufficient to provide the hair conditioning/styling/hold benefits desired considering the length and texture of the hair, and the type of product used. Preferably, the product is applied to wet or damp hair prior to drying and styling of the hair. After the compositions of the present invention are applied to the hair, the hair is dried and styled in the usual ways of the user.

The following examples further illustrate preferred embodiments within the scope of the present invention. The examples are given solely for the purposes of illustration and are not to be construed as limitations of the present invention as many variations of the invention are possible without departing from its spirit and scope.

The following table defines the silicone copolymers used in the examples (weight ratios given refer to proportion added to reaction mix):

| | |
|---|---|
| Copolymer #1 | 10/70/20 acrylic acid/n-butylmethacrylate/silicone macromer S2, polymer molecular weight about 100,000 |
| Copolymer #2 | 10/70/20 dimethylacrylamide/isobutyl methacrylate/silicone macromer S2, polymer molecular weight about 400,000 |
| Copolymer #3 | 60/20/20 diallyldimethyl ammonium chloride/isobutyl methacrylate/silicone macromer S1, polymer molecular weight about 500,000 |
| Copolymer #4 | 40/40/20 acrylic acid/methyl methacrylate/silicone macromer S1, polymer molecular weight about 400,000 |
| Copolymer #5 | 10/70/20 acrylic acid/n-butyl methacrylate/silicone macromer S1, polymer molecular weight about 300,000 |
| Copolymer #6 | 25/65/10 acrylic acid/isopropyl methacrylate/silicone macromer S2, polymer molecular weight about 200,000 |
| Copolymer #7 | 60/25/15 N,N-dimethylacrylamide/methoxyethyl methacrylate/silicone macromer S1, polymer molecular weight about 200,000 |
| Copolymer #8 | 12/64/4/20 N,N-dimethylacrylamide/isobutyl methacrylate/2-ethylhexyl methacrylate/PDMS macromer S1, polymer molecular weight about 300,000 |
| Copolymer #9 | 30/40/10/20 dimethylacrylamide/isobutyl methacrylate/2-ethylhexyl methacrylate/PDMS macromer S1, polymer molecular weight about 300,000 |
| Copolymer #10 | 80/20 t-butylacrylate/PDMS macromer S2, polymer molecular weight about 150,000 |

Silicone macromer S1- has a molecular weight of about 20,000 and is prepared in a manner similar to Example C-2c of U.S. Pat. No. 4,728,571, Clemens, issued Mar. 1, 1988.

Silicone macromer S2- has a molecular weight of about 10,000 and is prepared in a manner similar to Example C-2b of U.S. Pat. No. 4,728,571, Clemens, issued Mar. 1, 1988.

EXAMPLE I

The following is a hair spray composition representative of the present invention.

| Component | Weight % |
|---|---|
| Silicone Copolymer #4 | 2.00 |
| Ethanol | 72.90 |
| Perfume | 0.10 |
| Isobutane propellant | 25.00 |

This product is prepared by adding the silicone copolymer and perfume to the ethanol and mixing for several hours until all the polymer is dissolved. This "concentrate" is then placed in aerosol cans which are fitted with valves crimped under vacuum and then filled through the valve stem with isobutane dispensed by a pressure filler.

EXAMPLE II

The following is a shampoo composition representative of the present invention.

| Component | Weight % |
|---|---|
| Styling Agent | |
| Silicone Copolymer #2 | 1.00 |
| Chloropropyl heptamethyl cyclotetrasiloxane | 3.00 |
| Premix | |
| Silicone gum | 0.50 |
| Dimethicone, 350 cs. fluid | 0.50 |
| Main Mix | |
| Ammonium lauryl sulfate | 11.00 |
| Cocamide MEA | 2.00 |
| Ethylene glycol distearate | 1.00 |
| Xanthan gum | 1.20 |
| Kathon CG[1] | 0.04 |
| Citric acid to pH 4.5 | q.s. |
| Double reverse osmosis (DRO) H$_2$O | q.s. |

[1]preservative commercially available from Rohm & Haas

The Styling Agent and Premix are blended separately in a conventional manner. The Main Mix is prepared by first dissolving the xanthan gum in the water with conventional mixing. The remaining Main Mix ingredients are added and the Main Mix is heated to 15° F. with agitation for ½ hour. The Styling Agent and Premix are then added sequentially with about ten minutes agitation between additions, and the entire mixture is stirred while the batch is cooled to room temperature. For varied particle size, the Styling Agent and Premix can be added at different times using either or both high shear mixing (high speed dispersator) or normal agitation.

EXAMPLE III

The following is a shampoo composition representative of the present invention.

| Component | Weight % |
|---|---|
| Ammonium lauryl sulfate | 7.00 |
| Ammonium laureth sulfate | 7.00 |
| Cocamide MEA | 2.50 |
| Silicone Copolymer #3 | 1.00 |
| Natrosol 25OH[1] | 1.00 |
| Glydant[2] | 0.37 |
| DRO H$_2$O | q.s |

[1]hydroxyethyl cellulose commercially available from Aqualon Co.
[2]preservative commercially available from Glyco, Inc.

The shampoo is made by first dispersing the Natrosol and silicone copolymer in the water for about 1 hour with conventional agitation. The remaining ingredients are then added.

EXAMPLE IV

The following is a styling rinse composition representative of the present invention.

| Component | Weight % |
|---|---|
| Styling Agent Premix | |
| Silicone Copolymer #8 | 2.00 |
| Phenethylpentamethyl disiloxane | 6.00 |
| Octamethyl cyclotetrasiloxane | 3.00 |
| Xanthan Premix | |
| Xanthan gum | 0.25 |
| DRO H$_2$O | 25.00 |
| Main Mix | |
| Dihydrogenated tallow-dimethylamonium chloride (DTDMAC) | 0.50 |
| EDTA, disodium salt | 0.10 |
| D.C. 929[1] | 2.00 |
| Perfume | 0.10 |
| Poly Surf C[2] | 0.75 |
| Locust bean gum | 0.75 |
| Kathon CG[3] | 0.04 |
| DRO H$_2$O | q.s. |

[1]amodimethicone, commercially available from Dow Corning
[2]hydrophobically-modified hydroxyethyl cellulose, commercially available from Aqualon Co.
[3]preservative commercially available from Rohm and Haas The Styling Agent and Xanthan Premixes are blended separately in a conventional manner. The Main Mix is prepared by adding all the ingredients together and heating with agitation to 95° C. for about ½ hour. As the batch is cooled, the Styling Agent and Xanthan Premixes are added at about 60° C. with vigorous mixing. The batch is then cooled to ambient temperature.

EXAMPLE V

The following is a styling rinse composition representative of the present invention.

| Component | Weight % |
|---|---|
| Premix A | |
| Silicone Copolymer #3 | 2.00 |
| DRO H$_2$O | 10.00 |
| Premix B | |
| Silicone Copolymer #4 | 2.00 |
| DRO H$_2$O | 15.00 |
| NaOH solution (50%) | 0.20 |
| Main Mix | |
| Poly Surf C[1] | 1.00 |
| Stearamide DEA | 0.50 |
| Ethanol | 10.00 |
| Perfume | 0.20 |
| DRO H$_2$O | q.s. |

[1]hydrophobically-modified hydroxyethyl cellulose, commercially available from Aqualon Co.

Both premixes are blended separately in a conventional manner. The Main Mix is prepared by adding all the ingredients together and heating to about 60° C. with mixing. The premixes are then added to the Main Mix with agitation for about ½ hour and the batch is cooled to ambient temperature. Either sodium hydroxide or citric acid, if necessary, is added to adjust composition to pH 6.5.

EXAMPLE VI

The following is a hair grooming tonic composition representative of the present invention.

| Component | Weight % |
| --- | --- |
| Silicone Copolymer #9 | 0.70 |
| Perfume | 0.10 |
| Ethanol | q.s. |

The composition is made by mixing the above components together in a conventional manner.

EXAMPLE VII

The following is a shampoo composition representative of the present invention.

| Component | Weight % |
| --- | --- |
| Ammonium laureth sulfate | 7.00 |
| Cocamido propyl betaine | 6.00 |
| Silicone Copolymer #6 | 2.00 |
| Ethanol | 10.00 |
| PEG 150 distearate | 2.00 |
| Glydant[1] | 0.38 |
| Perfume | 1.00 |
| DRO H$_2$O | q.s. |

[1]preservative commercially available from Glyco, Inc.

The shampoo is prepared by combining the ammonium laureth sulfate (normally supplied as a 28% solution in water) and Silicone Copolymer and heating to 70° C. for about ½ hour with mixing. The remaining ingredients are added and mixed for an additional ½ hour. The batch is then cooled to ambient temperature. Composition pH is adjusted to 6.5 by the addition of citric acid or sodium hydroxide, if necessary.

EXAMPLE VIII

The following is a styling rinse composition representative of the present invention.

| Component | Weight % |
| --- | --- |
| Styling Agent | |
| Silicone Copolymer #5 | 3.00 |
| Phenylpentamethyl disiloxane | 9.00 |
| Premix | |
| Silicone Gum GE SE76[1] | 0.50 |
| Decamethyl cyclopentasiloxane | 4.00 |
| Main Mix | |
| Poly Surf C[2] | 0.60 |
| Locust bean gum | 0.50 |
| EDTA, disodium salt | 0.15 |
| DTDMAC | 0.65 |
| Glydant[3] | 0.40 |
| DRO H$_2$O | q.s. |

[1]Commercially available from General Electric
[2]hydrophobically-modified hydroxyethyl cellulose commercially available from Aqualon Co.
[3]preservative commercially available from Glyco, Inc.

The Styling Agent and Premix are blended separately by conventional means. The Main Mix is prepared by adding all the ingredients and heating to 95° C. for ½ hour with agitation. As the batch is cooled to about 60° C., the Premix and Styling Agent mix are added to the Main Mix with agitation and the batch is cooled to ambient temperature.

EXAMPLE IX

The following is a styling rinse composition representative of the present invention.

| Component | Weight % |
| --- | --- |
| Styling Agent | |
| Silicone Copolymer #10 | 3.00 |
| Octamethyl cyclotetrasiloxane | 9.00 |
| Premix | |
| Silicone Gum GE SE 76[1] | 0.50 |
| Decamethyl cyclopentasiloxane | 4.00 |
| Main Mix | |
| Poly Surf C[2] | 1.25 |
| Stearamide DEA | 0.40 |
| DTDMAC | 0.50 |
| Kathon CG[3] | 0.03 |
| Imidazole | 0.15 |
| Perfume | 0.10 |
| DRO H$_2$O | q.s. |

[1]Commercially available from General Electric
[2]hydrophobically-modified hydroxyethyl cellulose commercially available from Aqualon Co.
[3]preservative commercially available from Rohm & Haas The Styling Agent and Premix are blended separately by conventional means. The Main Mix is prepared by adding all the ingredients and heating to 95° C. for ½ hour with agitation. As the batch is cooled to about 60° C., the Premix and Styling Agent mixes are added to the Main Mix with agitation and the batch is cooled to ambient temperature.

EXAMPLE X

The following is a cold-wave hair perm composition representative of the present invention.

| Component | Weight % |
| --- | --- |
| Thioglycolic acid | 5.00 |
| Monoethanolamine | 6.00 |
| Silicone Copolymer #3 | 1.50 |
| PEG 10 monostearate | 0.50 |
| DRO H$_2$O | q.s. |

The composition is prepared by blending all the ingredients with agitation for about ½ hour at 60° C. and then cooling to ambient temperature.

EXAMPLE XI

The following is a hair conditioner composition representative of the present invention.

| Component | Weight % |
| --- | --- |
| Styling Agent Premix | |
| Silicone Copolymer #9 | 1.00 |
| Phenyl pentamethyl disiloxane | 4.00 |
| Silicone Premix | |
| Silicone gum, GE SE76[1] | 0.30 |
| Octamethyl cyclotetrasiloxane | 1.70 |
| Main Mix | |
| Cetyl alcohol | 1.00 |
| Quaternium 18[2] | 0.85 |
| Stearyl alcohol | 0.70 |
| Natrosol 250 MBR[3] | 0.50 |
| Ceteareth-20 | 0.35 |
| Fragrance | 0.20 |
| Dimethicone copolyol | 0.20 |

| Component | Weight % |
|---|---|
| Citric acid | 0.13 |
| Methylchloroisothiazolinone, methylisothiazolinone | 0.04 |
| Sodium chloride | 0.01 |
| DRO H$_2$O | q.s. |

[1] Commercially available from General Electric
[2] Ditallow quaternary ammonium compound, commercially available from Sherex
[3] hydroxyethyl cellulose material, commercially available from Aqualon Co.

The product is prepared by comixing all the Main Nix ingredients, heating to about 60° C. with mixing, and colloid milling down to about 45° C. At this temperature, the two premixes are added separately with moderate agitation and the batch allowed to cool to ambient temperature.

EXAMPLE XII

The following is a styling gel composition representative of the present invention.

| Component | Weight % |
|---|---|
| Silicone Copolymer #7 | 2.00 |
| Carbopol 940[1] | 0.75 |
| Triethanolamine | 1.00 |
| Dye solution | 0.05 |
| Perfume | 0.10 |
| Laureth-23 | 0.10 |
| DRO H$_2$O | q.s. |

[1] cross-linked polyacrylic acid, commercially available from B. F. Goodrich

This batch is made by mixing the listed components together in a conventional manner.

EXAMPLE XIII

The following is a hair mousse composition representative of the present invention.

| Component | Weight % |
|---|---|
| Silicone Copolymer #7 | 3.00 |
| Ethanol | 15.00 |
| Cocamine oxide | 0.60 |
| D.C. 190[1] | 0.20 |
| Cocamide DEA | 0.30 |
| Perfume | 0.10 |
| Isobutane | 7.00 |
| DRO H$_2$O | q.s. |

[1] dimethicone copolyol, commercially available from Dow Corning

The composition is made by blending all of the ingredients except isobutane at ambient temperature until well mixed. Aluminum aerosol cans are then filled with 95 parts of this batch, affixed with a valve which is crimped into position, and lastly pressure filled with 5 parts isobutane.

EXAMPLE XIV

The following is a pump hair spray composition representative of the present invention.

| Component | weight % |
|---|---|
| Silicone Copolymer #1 | 2.50 |
| Dibutyl phthalate | 0.20 |
| Phenyldimethicone | 0.30 |
| Perfume | 0.05 |
| Aminomethyl propanol | 0.20 |
| Ethanol | q.s. |

This composition is made by mixing the listed components together in a conventional manner.

When the compositions defined in Examples I–XIV are applied to hair in the conventional manner, they provide effective hair conditioning and styling/hold benefits without leaving the hair with a sticky/stiff feel.

What is claimed is:

1. A hair care composition comprising:
   (a) from about 0.1% to about 10.0% by weight of the composition of a block copolymer having one or more silicone block and one or more non-silicone blocks suitable for hair styling retention application, said copolymer having a weight average molecular weight of at least about 10,000 and being further characterized in that:
      (i) when dried the copolymer comprises a discontinuous phase which includes the silicone blocks and a continuous phase which includes the non-silicone blocks;
      (ii) the silicone blocks are covalently attached to the non-silicone blocks;
      (iii) the weight average molecular weight of each silicone block is from about 1,000 to about 50,000; and
      (iv) the nonsilicone blocks comprise monomers selected from the group consisting of acrylate monomers, vinyl monomers, and mixtures thereof; and
   (b) from about 0.5% to about 99.5% by weight of said composition of a carrier suitable for application to hair.

2. A hair care composition according to claim 1 wherein said silicone blocks comprise up to about 50% by weight of said copolymer.

3. A hair care composition according to claim 1 wherein said silicone blocks comprise from about 10% to about 20% by weight of said copolymer.

4. A hair care composition according to claim 1 wherein said silicone blocks are polydimethyl siloxane blocks.

5. A hair care composition according to claim 2 wherein said silicone blocks are polydimethyl siloxane blocks.

6. A hair care composition according to claim 3 wherein said silicone blocks are polydimethyl siloxane blocks.

7. A hair care composition according to claim 4 wherein said non-silicone blocks comprise acrylate monomers.

8. A hair care composition according to claim 4 wherein said non-silicone blocks comprise vinyl monomers.

9. A hair care composition according to claim 7 wherein said acrylate monomers are selected from the group consisting of t-butyl acrylate, acrylic acid, and mixtures thereof.

10. A method of conditioning and styling hair comprising applying to the hair an effective amount for conditioning and styling hair of a hair care composition comprising:
    (a) from about 0.1% to about 10.0% by weight of the composition of a block copolymer having one ore more silicone blocks and one or more non-silicone blocks suitable for hair styling retention application, said copolymer having a weight avenge molecular weight of at least about 10,000 and being further characterized in that:

(i) when dried the copolymer phase-separates into a discontinuous phase which includes the silicone blocks and a continuous phase which includes the non-silicone adhesive blocks;

(ii) the silicone portions are covalently attached to the non-silicone blocks; and (iii) the weight average molecular weight of each silicone block is from about 1,000 to about 50,000; and (iv) the nonsilicone blocks comprise monomers selected from the group consisting of acrylate monomers, vinyl monomers, and mixtures thereof; and (b) from about 0.5% to about 99.5%, by weight of the composition, of a carrier suitable for application to hair.

* * * * *

UNITED STATES PATENT AND TRADEMARK OFFICE
CERTIFICATE OF CORRECTION

PATENT NO. : 5,658,557
DATED : August 19, 1997
INVENTOR(S) : Raymond E. Bolich, Jr. and Peter M. Torgerson It is certified that error appears in the above-identified patent and that said Letters Patent is hereby corrected as shown below:

column 4, line 55 "about (40,000" should read --about 40,000--.

column 5, line 37 "-20° C. when" should read ---20° C. When--.

column 5, lines 52-53 "3,5,5,-trimethyl" should read --3,5,5-trimethyl--.

column 5, line 61 "n-buryl" should read --n-butyl--.

column 6, line 66 "r is integer" should read --r is an integer--.

column 7, line 16 "pollers" should read --polymers--.

column 10, line 17 "10.%" should read --10.0%--.

column 10, line 30 "amonium" should read --ammonium--.

column 11, line 11 "material s have" should read --materials have--.

column 11, line 11 "respect to the" should read --respective--.

column 14, line 7 "tetradecydimethylphosphine" should read --tetradecyldimethylphosphine--.

column 14, line 13 "dodecyldimethylphosphine" should read --dodecyldiethylphosphine--.

column 14, lines 13-14 "tetradecydimethylphosphine" should read --tetradecyldiethylphosphine--.

column 15, line 58 "Jun. 23, 3981" should read --Jun. 23, 1981--.

column 15, line 63 "phosphoium" should read --phosphonium--.

column 17, line 25 "catrate" should read --citrate--.

column 19, line 25 "15° F." should read --150° F.--.

column 20, line 9 "dimethylamonium" should read --dimethylammonium--.

UNITED STATES PATENT AND TRADEMARK OFFICE
CERTIFICATE OF CORRECTION

PATENT NO. : 5,658,557

DATED : August 19, 1997

INVENTOR(S) : Raymond E. Bolich, Jr. and Peter M. Torgerson

It is certified that error appears in the above-identified patent and that said Letters Patent is hereby corrected as shown below:

column 23, line 14 "Main Nix" should read --Main Mix--.

column 24, line 21 "silicone block" should read --silicone blocks--.

column 24, line 65 "avenge" should read --average--.

Signed and Sealed this

Thirty-first Day of March, 1998

Attest:

BRUCE LEHMAN

Attesting Officer

Commissioner of Patents and Trademarks